United States Patent [19]

Leinsing

[11] Patent Number: 5,676,346
[45] Date of Patent: Oct. 14, 1997

[54] NEEDLELESS CONNECTOR VALVE

[75] Inventor: Karl R. Leinsing, Raleigh, N.C.

[73] Assignee: IVAC Holdings, Inc., San Diego, Calif.

[21] Appl. No.: 705,062

[22] Filed: Aug. 29, 1996

Related U.S. Application Data

[63] Continuation of Ser. No. 442,025, May 16, 1995, abandoned.
[51] Int. Cl.$^6$ ..................................................... F16L 37/28
[52] U.S. Cl. ................... 251/149.1; 251/149.6; 604/256; 604/905
[58] Field of Search ........................... 251/149.1, 149.6; 604/256, 905

[56] References Cited

U.S. PATENT DOCUMENTS

| | | |
|---|---|---|
| 41,392 | 1/1864 | Parker . |
| 515,626 | 2/1894 | Strutzer et al. . |
| 558,848 | 4/1896 | Schäfer . |
| 584,091 | 6/1897 | Leidich . |
| 2,212,733 | 8/1940 | Grigsby ................... 251/5 |
| 2,342,192 | 2/1944 | Grigsby ................... 285/71 |
| 2,371,434 | 3/1945 | Eppler ..................... 51/12 |
| 2,585,527 | 2/1952 | Adams ................... 222/490 |

(List continued on next page.)

FOREIGN PATENT DOCUMENTS

| | | |
|---|---|---|
| 2083670 | 5/1993 | Canada . |
| 884 441 | 7/1953 | Germany . |
| 25 11 844 | 9/1975 | Germany . |
| WO93/11828 | 6/1993 | WIPO . |

*Primary Examiner*—A. Michael Chambers
*Attorney, Agent, or Firm*—Fulwider Patton Lee & Utecht, LLP

[57] ABSTRACT

A valve mechanism for a needleless connector employs a deformable piston having a piston head of elliptical cross-section with a marquise-shaped bore formed along its longitudinal axis wherein the major axes of the respective generally elliptical shapes are oriented perpendicular to one another. The piston head is captured within the connector housing and is reciprocal between a section of reduced diameter adjacent the connection port and a section of enlarged diameter. Constraining the piston head into the section of reduced diameter causes the elliptical bore to be squeezed shut while positioning the piston head in the section of enlarged diameter causes the piston head to relax and assume its natural elliptical shape, while the bore similarly regains its natural open shape to provide a fluid path therethrough. A compressible or extendible section affixed to the piston head serves to bias the piston into the section of reduced diameter. A tapered section of the piston contacts the housing to secure the top of the piston flush with the top of the housing for ease in cleaning.

29 Claims, 6 Drawing Sheets

U.S. PATENT DOCUMENTS

| | | | |
|---|---|---|---|
| 3,002,660 | 10/1961 | Taylor | 222/490 |
| 3,349,972 | 10/1967 | Whitford | 222/212 |
| 3,490,732 | 1/1970 | Leroy | 251/5 |
| 3,624,800 | 11/1971 | Swick | 251/4 |
| 3,823,840 | 7/1974 | Zackheim . | |
| 3,837,381 | 9/1974 | Arroyo . | |
| 3,853,127 | 12/1974 | Spademan | 128/214.4 |
| 3,965,925 | 6/1976 | Gooch | 137/451 |
| 3,977,400 | 8/1976 | Moorehead | 128/214.4 |
| 4,244,478 | 1/1981 | Handman | 215/249 |
| 4,334,551 | 6/1982 | Pfister . | |
| 4,475,548 | 10/1984 | Muto | 128/207.14 |
| 4,655,752 | 4/1987 | Honkanen et al. . | |
| 4,752,287 | 6/1988 | Kurtz et al. . | |
| 4,809,679 | 3/1989 | Shimonake et al. . | |
| 4,867,198 | 9/1989 | Faust | 137/503 |
| 4,874,377 | 10/1989 | Newgard et al. . | |
| 5,053,013 | 10/1991 | Ensminger et al. | 604/167 |
| 5,064,416 | 11/1991 | Newgard et al. | 604/167 |
| 5,071,017 | 12/1991 | Stull | 215/260 |
| 5,080,654 | 1/1992 | Picha et al. . | |
| 5,100,394 | 3/1992 | Dudar et al. . | |
| 5,108,380 | 4/1992 | Herlitze et al. . | |
| 5,122,123 | 6/1992 | Vaillancourt | 604/192 |
| 5,125,903 | 6/1992 | McLaughlin et al. | 251/149.1 |
| 5,135,489 | 8/1992 | Jepson et al. . | |
| 5,188,620 | 2/1993 | Jepson et al. . | |
| 5,199,948 | 4/1993 | McPhee . | |
| 5,201,717 | 4/1993 | Wyatt et al. | 604/192 |
| 5,201,725 | 4/1993 | Kling . | |
| 5,203,775 | 4/1993 | Frank et al. | 604/256 |
| 5,211,638 | 5/1993 | Dudar et al. . | |
| 5,215,538 | 6/1993 | Larkin | 251/149.1 |
| 5,242,393 | 9/1993 | Brimball et al. . | |
| 5,251,873 | 10/1993 | Atkinson et al. | 251/149.1 |
| 5,269,771 | 12/1993 | Thomas et al. . | |
| 5,295,657 | 3/1994 | Atkinson . | |
| 5,295,658 | 3/1994 | Atkinson et al. . | |
| 5,300,034 | 4/1994 | Behnke et al. . | |
| 5,326,534 | 7/1994 | Yamazaki et al. | 422/102 |
| 5,354,275 | 10/1994 | Behnke et al. | 604/86 |
| 5,487,728 | 1/1996 | Vaillancourt | 604/86 |
| 5,501,426 | 3/1996 | Atkinson et al. | 251/149.1 |
| 5,501,676 | 3/1996 | Niedospial et al. | 604/283 |
| 5,509,912 | 4/1996 | Vaillancourt et al. | 604/283 |
| 5,514,116 | 5/1996 | Vaillancourt et al. | 604/283 |

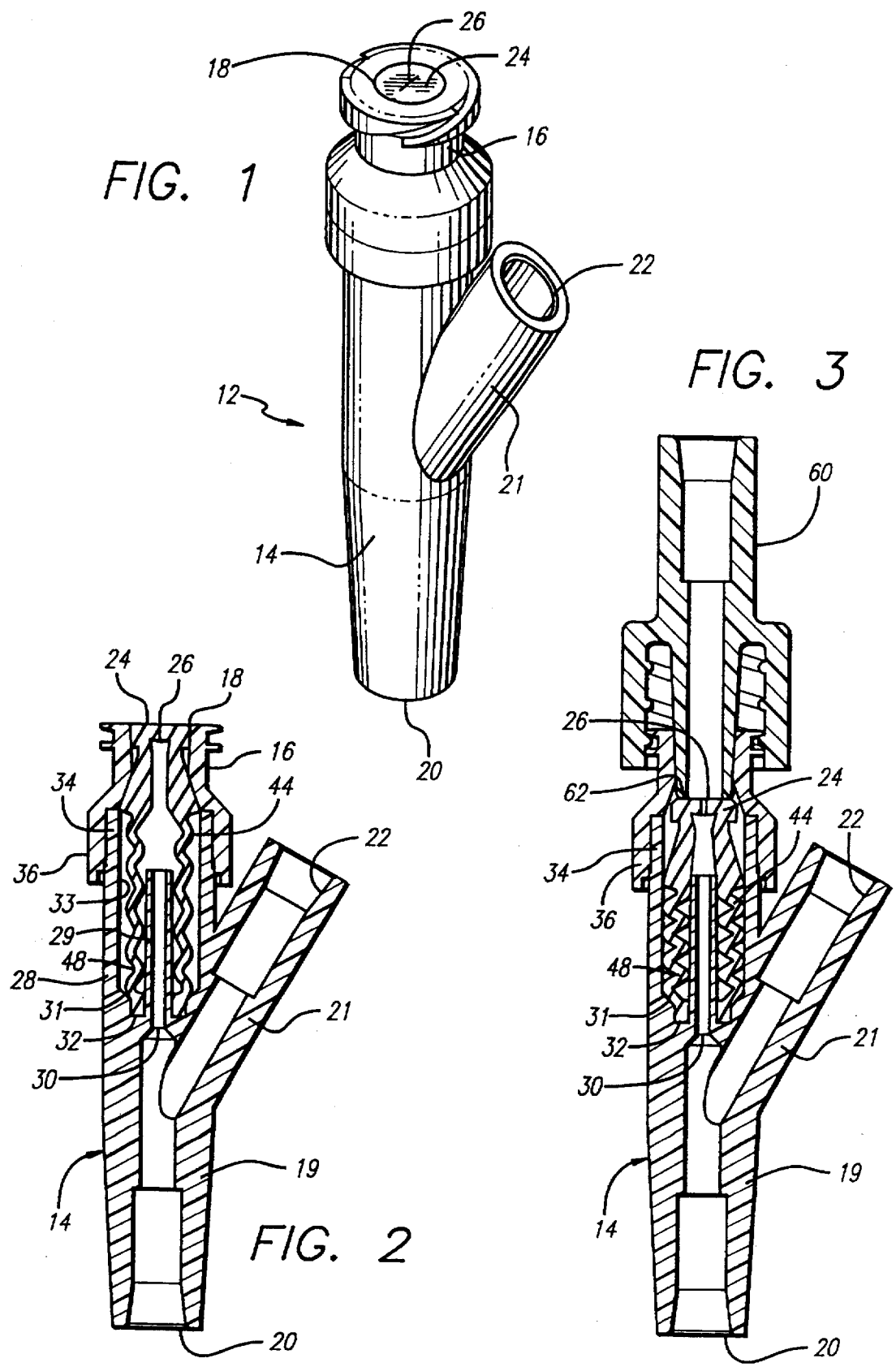

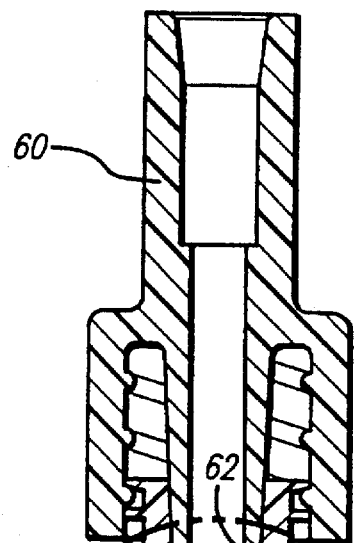
FIG. 8a
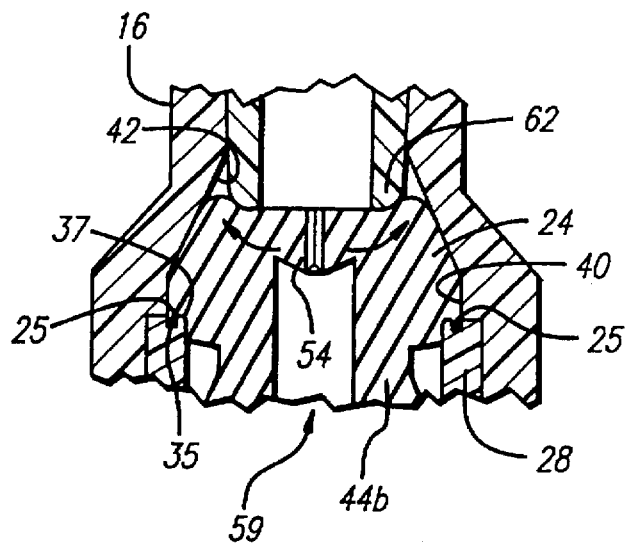
FIG. 8b
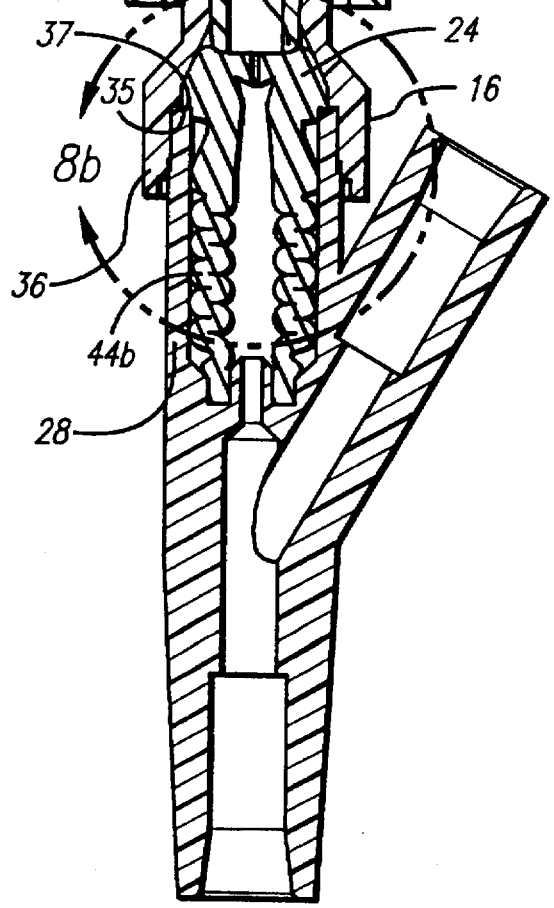
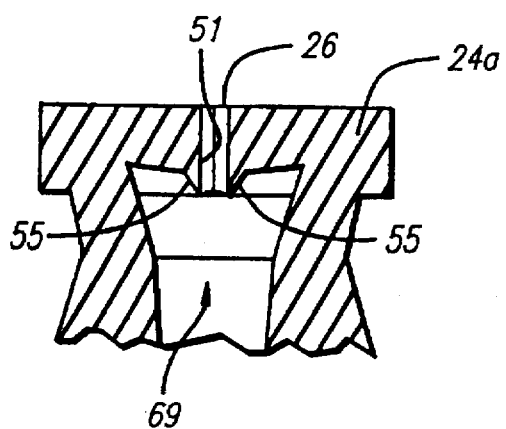
FIG. 9

NEEDLELESS CONNECTOR VALVE

This is a continuation of application Ser. No. 08/442,025 filed May 16, 1995, now abandoned.

BACKGROUND

The invention relates generally to connectors of the type used in the handling and administration of parenteral fluids, and more particularly, to a valve mechanism incorporated within such connector for enabling a fluid interconnection to be made therewith without the use of a sharp cannula.

Injection sites for injecting or removing fluid from a system, such as an IV infusion set connected to a patient, or a fluid reservoir or drug vial, are well known and widely used. Conventional injection sites generally involve a pierceable septum formed of an elastomeric material such as latex rubber or the like, captured in an access port. The housing of the septum may, for example, be the Y-body of a conventional Y-site component of an IV delivery set. A sharp cannula is inserted into the access port piercing the septum to position the distal, open end of the cannula past the septum to make fluid connection with the interior of the access port. Upon withdrawal of the sharp cannula, the elastomeric septum reseals itself thus maintaining a sterile environment within the housing of the injection site. The outer surface of the septum of the injection site is wiped with an antiseptic before each use to prevent septic agents from being drawn into the access port by the piercing movement of the needle.

More recently, connectors for accommodating the injection and withdrawal of fluids without the use of sharp cannulas have been put to use in increasing numbers. This is due, at least in part, to concern regarding the possibility of the transmission of blood-borne diseases through accidental needle punctures of persons handling the sharp cannulas. Connectors having no sharpened surfaces are desirable because such hazard is thereby eliminated.

However, some existing needleless connectors suffer from various shortcomings. For example, relatively complex configurations employing a large number of parts are difficult to manufacture and assemble. This not only increases costs but may pose problems in service. Additionally, complex systems may not be intuitive to use which may prove distracting and therefore undesirable in the typical hospital room environment.

A further concern in the design of needleless connectors is the order of events in which the connection is made. For example, allowing fluid to escape or air to enter during interconnection due to the female connector being opened before the male connector is sufficiently seated is undesirable.

Additionally, some existing connectors accommodate a relatively large interior fluid volume requiring the injection of a commensurately large volume of fluid just to fill and prime the connector. If not taken into account, this fluid volume can detract from the volume of medicament injected into the patient and may be clinically significant. An inconvenient separate flushing procedure may be required in low dose injections or in the injection of unstable medicines due to this relatively large interior volume. Moreover, relatively complex geometries and the use of springs and the like in the wetted portion of the connector interior may give rise to "dead spaces" where fluid tends to linger due to poor flushing. Dead spaces give rise to problems similar to those occasioned by large interior volumes, again resulting in the inconvenient requirement of flushing.

Where metal components, such as metallic springs, are used in connectors, the metal components can interfere with magnetic resonance imaging used in hospitals. A further difficulty with the use of coiled metallic springs is the care that must be taken during manufacture. Allowing coiled springs to come into contact with each other while awaiting assembly into the valves may result in the springs becoming entangled with each other necessitating further handling before they can be installed.

Furthermore, it is desirable that needleless connectors be configured so that they can be easily cleaned by an antiseptic wipe, or otherwise sterilized, prior to making a connection. All exterior surfaces that may be involved in the transmission of fluid should be readily available for cleaning prior to the connection being made. Some prior connectors have a small rift or fissure defined by a clearance between parts. Such a feature is difficult and inconvenient to clean in attempting to sterilize a connector. Alternatively, connectors requiring a cap to maintain a sterile connection port prior to use are undesirable because the extra steps involved in removing and replacing a cap are inconvenient, while the manufacture of the cap adds expense.

The ability to accommodate a high fluid flow rate is also desirable in a needleless connector. Physicians in certain situations order the administration of medicaments at high flow rates. Some prior connectors have restrictive geometries that limit their flow capacity such that administering fluids at high rates is impossible. The use of tortuous flow paths through a connector or multiple openings through a movable valve device through which the fluid must flow can result in a reduction of the maximum rated flow rate for the connector. With some restrictive geometries, higher flow rate requirements may not be possible under gravity head flow conditions and a positive pressure pump may be needed. Such connectors would be undesirable where pumps are not available and the usefulness of such connectors would be severely limited. The increase of flow rate capability and elimination of the tortuous fluid path can also facilitate priming of the connector and reduce potential blood hemolysis.

In addition, the performance of connectors incorporated into IV administration sets and used to allow automatic piggyback administration of medicaments becomes degraded when high flow rates through the connector cannot be accommodated. If high flow rates through the connector cannot be accommodated, automatic piggyback rates using infusion pumps must be limited to relatively low infusion rates. Otherwise, accidental simultaneous flow of primary fluids may occur when normal head height differentials are used between the primary and piggyback containers. Higher flow rates through the needleless connector allows higher flow rates of automatic piggyback administration without the possibility of accidental simultaneous flow of primary fluids.

A further consideration in the design of a connector is its compatibility with other connectors. In those cases where a cannula is mounted internally in a needleless connector to slide inside the fluid port of a male connector inserted into the needleless connector to establish the flow path, the outer diameter of that cannula must be closely controlled so that it can successfully mate with a wide range of male connectors. Making it too large may result in interference with certain male connectors thus rendering them unusable with the needleless connector. However, making the outer diameter of the cannula too small results in reduced fluid flow rates through the cannula.

Additionally, the internal cannula in the connector can damage the valve itself. In particular, the cannula can pierce, cut, or tear a rubber piston or septum mounted over it and damage the resealability of the valve. The cannula could also create particulate by tearing off portions of the rubber piston or septum when a male luer is inserted into the connector. This may occur where the bore of the male luer interferes with or is closely sized with the cannula and creates a punching action that removes a piece of the rubber septum. Consequently, it is desirable to avoid such configurations.

Hence, those concerned with the development of connectors have recognized the need for an improved needleless connector that has a relatively simple construction with a small number of parts, that avoids the entry of air when the initial connection is made, that has reduced flushing requirements, that can be easily cleaned prior to use, and that permits a relatively high fluid flow rate. The present invention fulfills such needs and others.

SUMMARY OF THE INVENTION

Briefly, and in general terms, the invention is directed to a needleless connector incorporating a valve therein that is constructed of a small number of parts of relatively simple design, is relatively inexpensive to manufacture, is easy and intuitive to use, is easily cleaned, and does not require a protective cap. Moreover, a device in accordance with the invention accommodates a relatively high flow rate and has minimal interior fluid volume and "dead space."

More specifically, the connector of the present invention comprises a hollow housing having a connection port, an exit orifice, a first section of a first preselected cross-sectional shape and size disposed adjacent the connection port, and a second section of a second preselected cross-sectional shape and size. A deformable piston head having a bore is received within the housing so as to be movable between the first and second sections. Positioning the piston head within the first section causes it to be deformed so as to occlude the bore while positioning the piston head within the second section allows the piston head to assume its un-deformed state in which the bore is open to provide a fluid flow path between the connection port and the exit orifice. Additionally, the connector comprises means for biasing the piston head into the first section so that the bore is occluded.

In further aspects, the piston head is elliptical in cross-section and the first section of the housing is circular in cross-section. Additionally, the bore formed in the piston head has a marquise-shaped cross-section, i.e., of pointed elliptical cross-section shape when the piston head is in its un-deformed state, having its major axis oriented perpendicularly to the major axis of the elliptical cross-section of the piston head.

In another aspect, the piston is an element comprising a rubber molding that simultaneously serves multiple functions. The top part of the piston element includes the piston head that is elliptical in shape and has the marquise-shaped bore formed along its longitudinal axis. The marquiseshaped bore and the elliptical outer shape of the piston head are oriented in relation to each other such that the major axes of their respective elliptical shapes are perpendicular to one another. The piston head is connected to a resilient bottom part of the piston element that is generally accordioned in shape and collapsible. The bottom part thus functions as a compression spring that urges the piston head into the first section of the housing. Additionally, the interior of the entire piston element serves as a fluid path. Alternatively, the bottom part of the piston element may be formed as an extension spring, such as a diaphragm.

In a further aspect, the bore diameter of the housing steps down near the connection port such that the normally elliptical piston head, when received therein, is compressed into a circular cross-section thereby causing the marquise-shaped bore to be squeezed shut. The spring action provided by the collapsible accordioned end of the piston or by the stretchable diaphragm configuration serves to bias the piston head toward the connection port to maintain it in its closed configuration.

In yet a further aspect, the piston element includes a tapered ramp/lock section that engages a portion of the housing to limit the movements of the piston so that it is flush with the connection port in the closed configuration. In this position, the smooth flat top surface of the piston head is flush with the connection port thereby eliminating the possibility of pooling between the piston and the housing and rendering the device easier to disinfect.

In yet a further aspect, a taper lip seal located under the piston head and about the piston bore seals the bore so that it can withstand substantial internal pressures.

In additional more detailed aspects, as an external fluid conduit device, such as a male luer, is brought into contact with the top surface of the piston head, a seal is formed even before the fluid path into the piston and housing is opened to prevent any fluid from leaking out or air leaking in. Upon further insertion of the male luer into the housing, the piston head is pushed into the housing against the bias provided by its accordioned section. This causes the piston head to be positioned within a section of enlarged diameter in the housing thereby allowing the piston head to assume its natural elliptical state which causes its marquise-shaped bore to open. A fluid path is thereby opened through the piston head, through the interior of the accordioned section of the piston and into the distal section of the housing without the need for the male luer to penetrate into or through the piston head.

In further aspects, the distal section of the housing may comprise a Y-site, J-loop, T-connector, PRN adapter, or any of a variety of other configurations.

These and other features and advantages of the present invention will become apparent from the following detailed description of preferred embodiments which, taken in conjunction with the accompanying drawings, illustrate by way of example the principles of the invention.

BRIEF DESCRIPTION OF THE DRAWINGS

FIG. 1 is a perspective view of a connector incorporating principles of the present invention;

FIG. 2 is an enlarged cross-sectional view of the connector shown in FIG. 1 in its closed position;

FIG. 3 is an enlarged cross-sectional view of the connector shown in FIG. 2 with a male connector inserted in the connector's connection port thereby moving the piston of the connector to its open position;

FIG. 8a is a cross-sectional view of an alternative embodiment of a connector incorporating principles of the invention;

FIG. 8b is a further enlarged cross-sectional view of a portion of the connector of FIG. 8a showing the piston with an inserted male connector;

FIG. 9 is a greatly enlarged cross-sectional view of an alternative embodiment piston head;

FIG. 11b presents the view of FIG. 11a taken along lines 11b—11b;

DETAILED DESCRIPTION OF PREFERRED EMBODIMENTS

Figure 6:
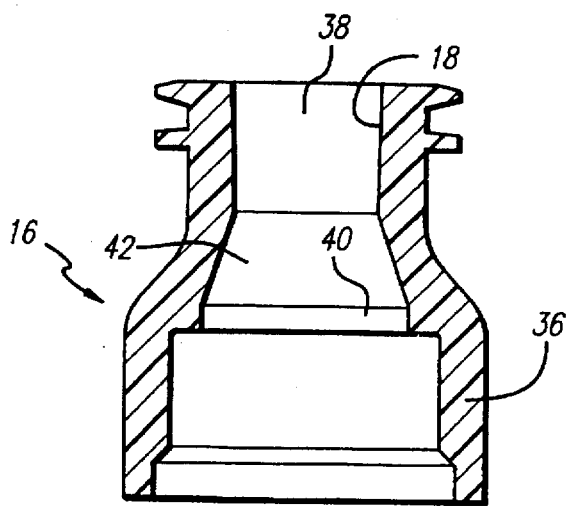
FIG. 6 is a further enlarged cross-sectional view of the luer adapter component of the connector shown in FIGS. 1 through 5.

Referring now to the drawings in which like numerals refer to like or corresponding elements among the several figures, there is illustrated in FIGS. 1 through 3 a Y-connector incorporating a needleless valve embodying the principles of the present invention. This particular connector configuration was selected for illustration purposes only as the subject needleless valve can be embodied in any of a variety of connectors including, but not limited to, J-loops, T-Connectors, Tri-connectors, PRN adapters, luer-locks, slip luers, tubing engagement devices, access pins, and others.

As is shown in FIG. 1, the Y-connector 12 comprises a housing 14 terminating in an exit port 20 and having a Y-branch 21 with a Y-branch port 22. This particular embodiment also comprises a luer adapter 16 forming a part of the housing and that adapter includes a connection port 18. The adapter is configured to receive all ANSI standard male luer fittings, as well as other blunt cannulas or fluid conduit devices. In its unaccessed state or closed position, a piston head 24 located internally to the housing is flush with the surrounding connection port 18 and has a tightly closed orifice 26 at its center.

FIG. 2 shows in enlarged cross-section the Y-connector of FIG. 1 with the needleless valve in its closed position. The Y-branch 21 leads to the Y-branch port 22 and the distal section 19 of the housing 14 extends between the Y-branch and the exit port 20. The housing 14 includes a tubular section 28 having a circular cross-section, an exit orifice 30 at its base 31, a support tube 29 extending upwardly from the base, and a groove 32 formed in the base surrounding the support tube. The exterior surface of the tubular section 28 near its proximal end is stepped slightly inwardly 34 to receive the luer adapter 16 thereover and provide ultrasonic weld geometry. Alternatively, the adapter and the housing may be joined by a spin weld, snap fit, by bonding, or by other means.

Figure 4:
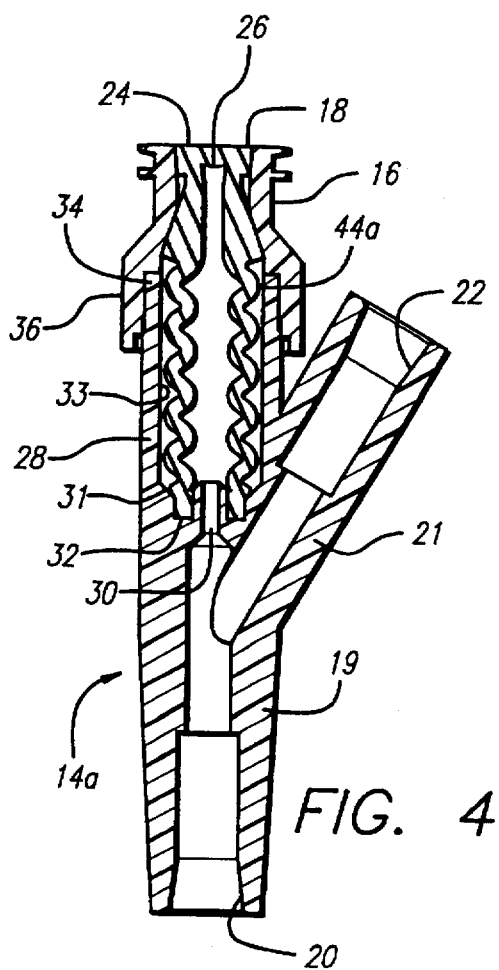
FIG. 4 is a cross-sectional view of another embodiment of a connector incorporating principles of the invention and showing it in its closed position.
Figure 5:
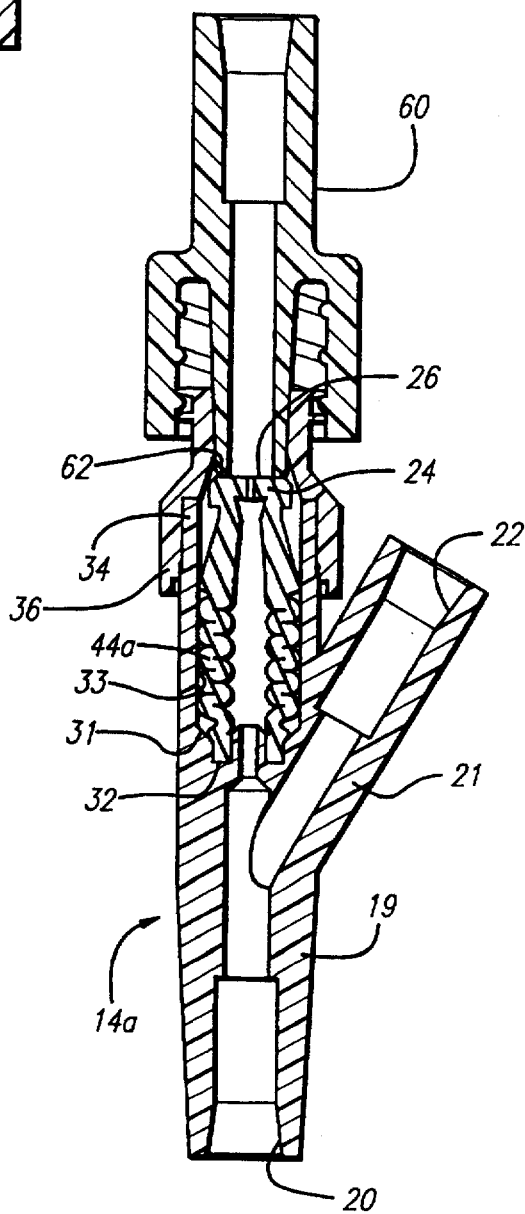
FIG. 5 is a cross-sectional view of the connector shown in FIG. 4 with a male connector inserted in the connector's connection port thereby moving the piston of the connector to its open position.

FIG. 2 additionally shows the piston element 44 in place within the bore 33 of the tubular section 28 captured between the luer adapter 16 and the base 31. The piston element 44 includes a total of four bellows. The alternative embodiment illustrated in FIGS. 4 and 5 is similar to the embodiment shown in FIGS. 2 and 3, with the exception that the support tube 29 has been deleted, and the piston element 44a has a total of five bellows of shallower angle.

As is illustrated in FIG. 6, the interior of the luer adapter 16 has sections of various diameters. The section directly adjacent the connection port 18 comprises a standard ANSI luer taper section 38 that incorporates a very slight inward taper. The center section 40 has a substantially larger diameter and is separated from the taper section 38 by the tapered ramp/lock section 42. Additionally, the inner diameter of the center section 40 is slightly larger than the inner diameter of the tubular section 28 of the body 14 for reasons discussed below. Finally, the luer adapter 16 includes a skin 36 that is dimensioned to fit over the stepped proximal end 34 of the tubular section 28 to provide ultrasonic weld geometry. The adapter 16 may be molded of a material containing a phosphorescent colorant to render the connector visible in a darkened room.

As is generally shown in FIGS. 2 through 5, a resiliently deformable piston element 44 and 44a is captured between the base 31 of the tubular section 28 and the luer adapter 16 in the bore 33 of the housing 14. While the details of its structure vary slightly from embodiment to embodiment, the views of element 44a shown in FIGS. 7a and 7b serve to illustrate many of the common features. The piston element's structure 44a which is molded in its entirety of rubber in this embodiment generally includes a piston 46 and a compressible section 48. The piston 46, in turn, includes a piston head 24 that is elliptical in cross-section and a thick taper-lock portion 50 that is circular in cross-section. A marquise-shaped bore 51 is formed along the longitudinal axis of the piston head 24 and terminates in an orifice 26 at its proximal end and a taper lip seal 59 at its distal end. The taper lip seal 59 comprises a pair of lips 54 that extend from opposed sides of the bore's sides. The lips comprise conical sections that extend from the bore's sides to function as a seal. The angle of the taper is selected so that internal pressure existing in the valve when the piston is in the closed state would force the lips toward one another thereby holding the bore closed.

Figures 7A, 7B:
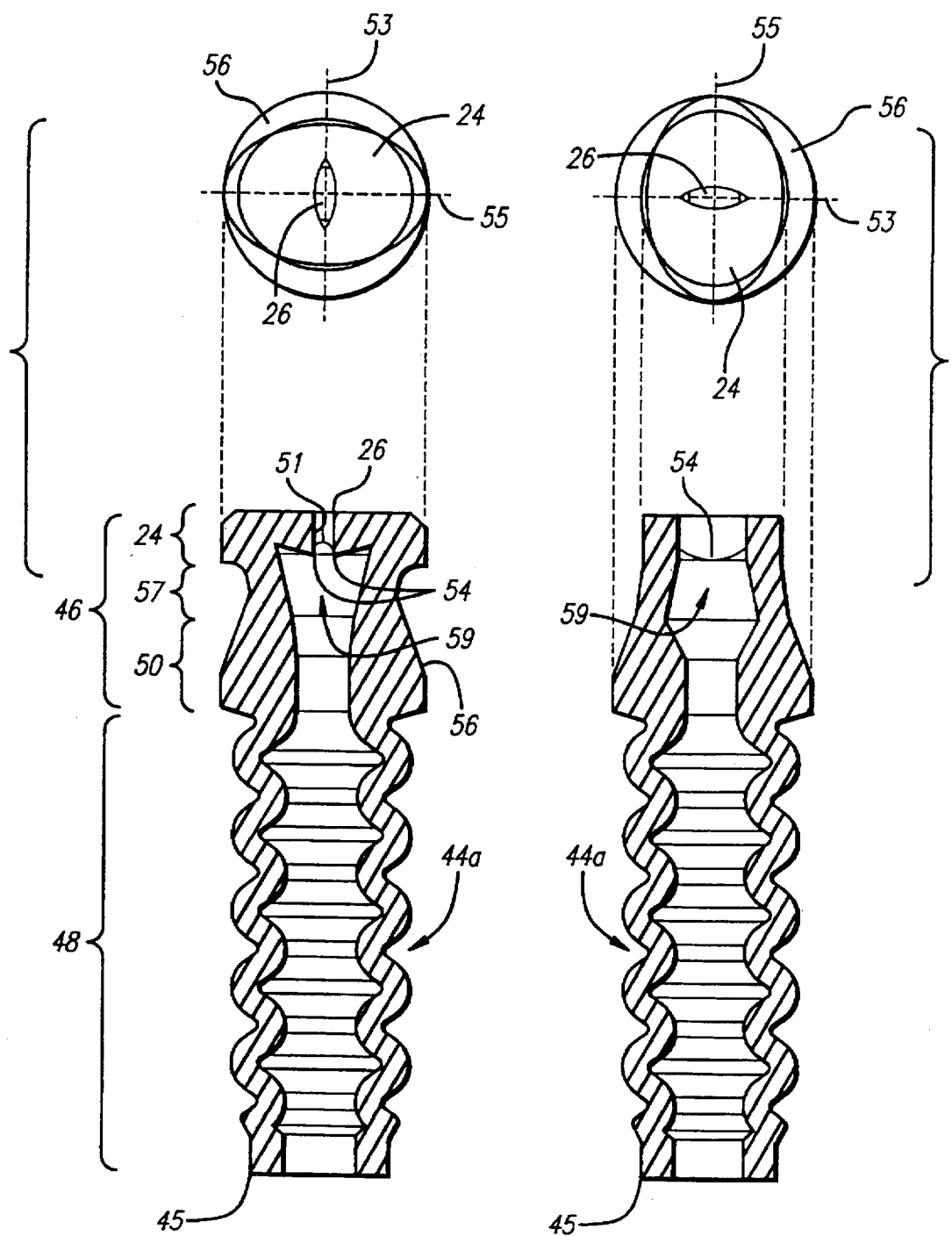
FIGS. 7a and 7b are further enlarged cross-sectional side and top views of the piston component of the connector shown in FIG. 2 with the views rotated 90° from each other.

As is apparent when comparing FIGS. 7a and 7b, the marquise-shaped bore 51 is oriented such that its major axis 53 is perpendicular to the major axis 55 of the elliptically-shaped piston head. Additionally, the transitional section 57 between the piston head 24 and the taper lock portion 50 is elliptical and conical in shape wherein the major axis of such ellipse is parallel to the major axis 55 of the piston head and perpendicular to the major axis 53 of the bore 51. This geometry further assists in naturally biasing the marquise-shaped bore into its open position. This elliptical shape creates an outward force parallel to the major axis of the elliptical shaped piston head and an inward force parallel to the minor axis. The inward force tends to compress the piston in a direction perpendicular to its major axis and thus tends to pull the marquise-shaped bore open when a male luer applies force to the top of the piston moving the piston into the center section 40 of the adapter 16.

The taper-lock portion 50 of the piston element 44 is fairly thick in order to prevent it from being compressed. This thicker section helps to hold the piston in the valve at higher internal pressures and also acts as a divider between the spring action below and the opening and closing of the marquise-shaped bore above. Although the piston element 44 is seated in the base 31 of the housing tightly, extreme internal pressures may provide a substantial force to push the piston element 44 out of the housing 14 thereby destroying its integrity. This thickened portion 50 of the piston element provides added assurance that it will not compress under such internal forces and will hold the piston in position in the housing.

FIGS. 8a and 8b illustrate an alternative embodiment wherein the inner diameter of the tubular section 28 is sufficiently reduced relative the inner diameter of the center section 40 of the adapter 16 to accommodate an annular groove 35 formed in its proximal edge. Sections of a circular groove 37 are formed on each end of the major axis 55 of the bottom of the elliptical piston head 24 to provide hooks 25. The hooks are configured so as to engage the groove 35 in the tubular section. Once the hooks have engaged the groove as a result of the male luer 62 pushing the piston 24 farther into the adapter 16, the hooks will oppose further movement of the periphery of the piston and will result in any further male luer forces causing the bore 51 to open wider, as shown in FIG. 8b.

FIG. 9 illustrates an alternative embodiment wherein a pair of flexible flaps 55 extend from about the bore 51 to improve the internal pressure handling capability of the piston 24. The angle of the flaps is selected so that internal pressure existing in the valve when the piston is in its closed state would force the flaps toward one another thereby holding the bore 51 closed. In another embodiment the flaps may be made thinner and longer. They may then function as a check valve when the piston is in its open state.

Returning now to FIGS. 7a and 7b, the bore 51, in conjunction with the hollow interior of the taper lock section 50 and the hollow interior of the compressible section 48, forms a fluid path through the entire piston element 44. The compressible section 48 may comprise an accordioned configuration as shown in FIGS. 2–5, 7a, 7b, and 8a or, alternatively, an annularly or helically ribbed structure that similarly allows for the controlled collapse of the structure along its longitudinal axis to generate a restoring force. Some alternative embodiments are illustrated in FIGS. 10a through 10d and show possible variations in the number, size, and configuration of the ribs or bellows. Different shapes of the piston element may be used to improve flow rate, activation force, spring return rate, sealing, piston retention, and acceptance of blunt cannulas. The piston geometry variations could also improve the valve function with fluids that easily solidify by removing internal annular grooves and pinch point areas. Modifications include changing the number of bellows, ribs, wall thickness, height, diameter, durometer, color, and geometry. Pinch point areas are formed from the accordioned folds that come together upon compression of the piston and could, under certain conditions, trap solidified fluids to interfere with the compression of the piston.

Figure 10A:
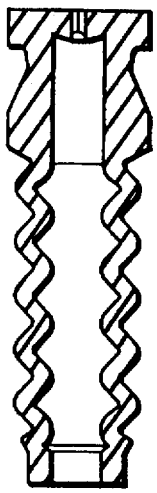
FIGS. 10a through 10d present different configurations of a piston element usable in a connector of the present invention.
Figure 10B:
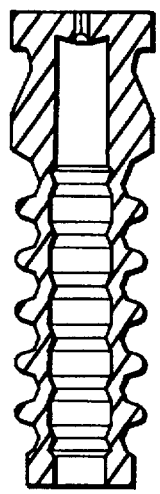
Figure 10C:
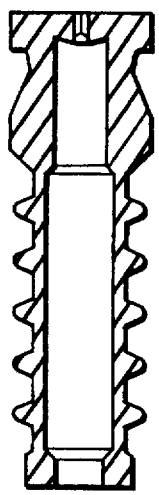
Figure 10D:
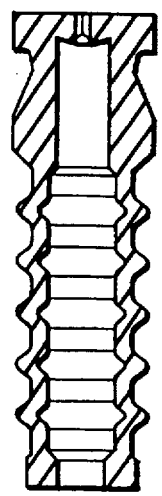

In particular, FIG. 10a shows a compressible section having five bellows as per FIGS. 4, 5, 7, and 8 which require a reduced activation force. FIG. 10b shows a compressible section having an external ribbed structure wherein the compressed shape has no pinch points. FIG. 10c shows the compressible section of the piston element with straight walls to increase activation force and reduce pinch points. FIG. 10d shows a compressible section which provides a smooth interior surface upon compression to increase the flow rate.

Returning again to FIGS. 2, 3, 7a, and 7b, the distal end 45 of the compressible section 48 is received in the groove 32 in the base 31 of the tubular section 28 to form a tight seal about the support tube 29 and the exit orifice 30. The piston element is lubricated with FDA approved silicone oil to facilitate movement of the piston within the connector and to prevent the bore 51 through the piston head 24 from being sealed closed during sterilization.

Figure 11A:
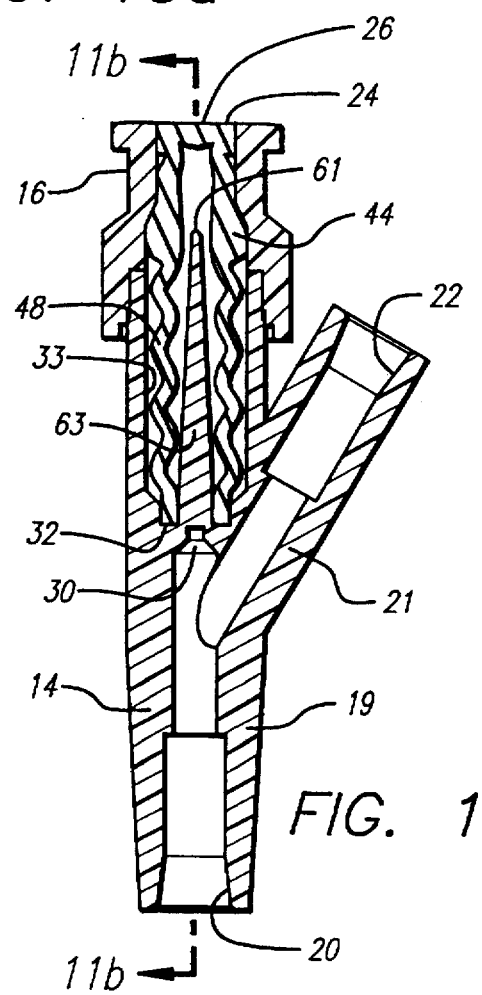
FIGS. 11a and 11b illustrate cross-sectional views of an alternative embodiment of a connector incorporating principles of the present invention in which a center post is included.
Figure 11B:
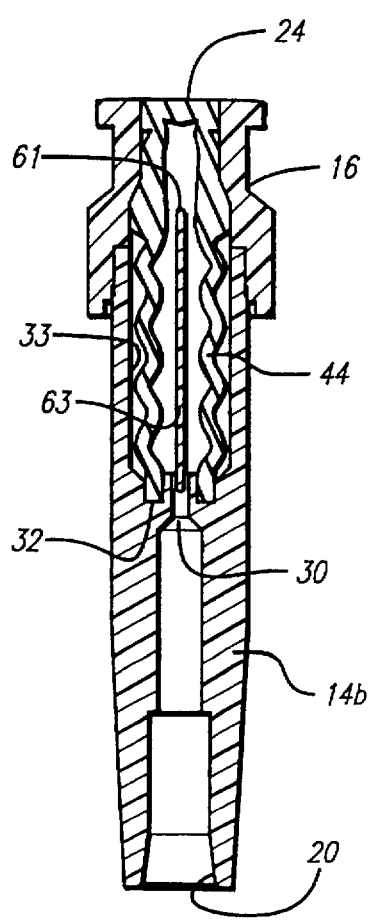

In the alternate embodiments illustrated in FIGS. 11a and 11b a support structure, in the form of a flattened post 63, has been added to the interior of the tubular section 28 so as to project into the compressible section 48 of the piston 46. The post has a rounded tip 61 that extends into the bore 51 of the piston element 24 upon depression of the piston 44 to assist in its opening. Clearance between the post's tip 61 and the pointed ends of the marquise-shaped bore 51 facilitates flow thereby, while clearance between the thinner dimension of the flattened post 63 and the interior surface of the collapsible section 48 allows for the flow of fluid into the exit orifice 30.

Figure 12:
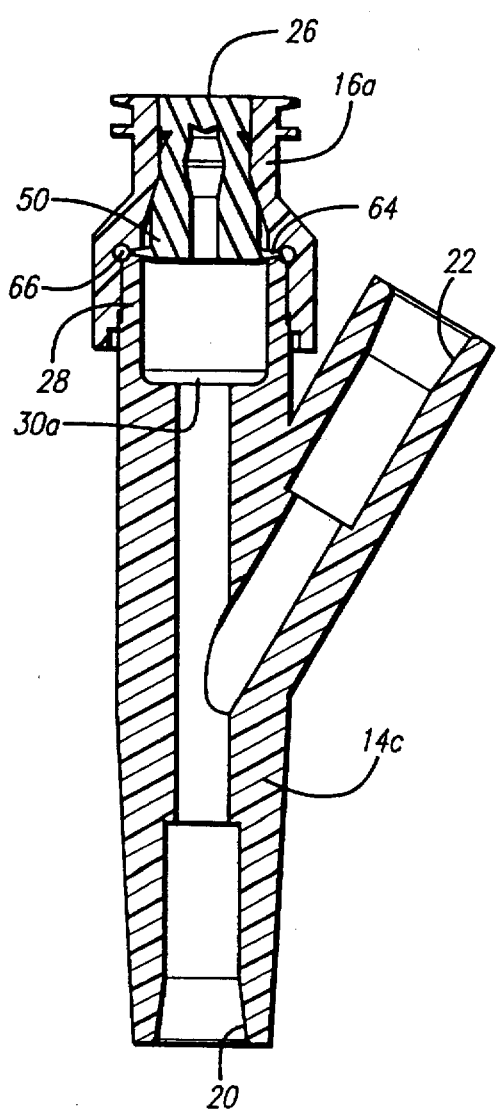
FIG. 12 is an enlarged cross-sectional view of another alternative embodiment of a connector in accordance with aspects of the invention.
Figure 13:
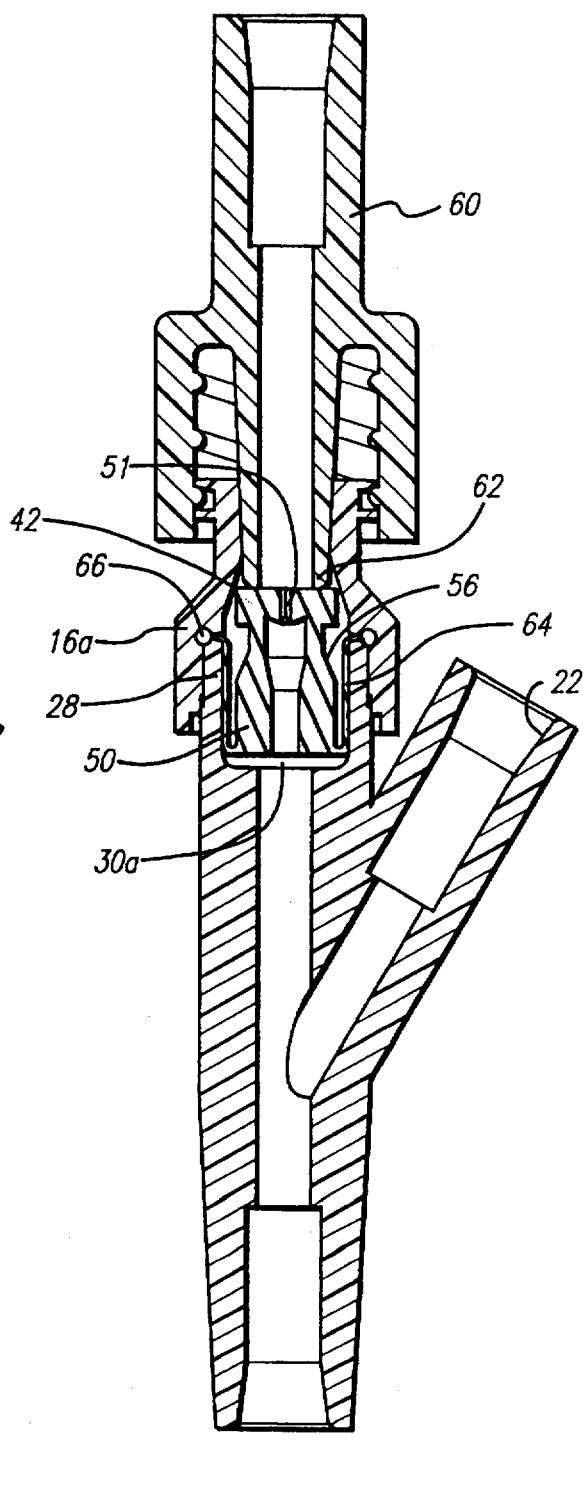
FIG. 13 is an enlarged cross-sectional view of the connector shown in FIG. 12 with a male connector inserted for fluid communication.

FIGS. 12 and 13 illustrate a further alternative embodiment wherein an extension spring in the form of a diaphragm 64 serves to bias the piston 46 into its closed position, rather than the compression spring approach shown in the other figures. The diaphragm 64 extends from the base of the taper lock section 50 and has an annular bead 66 formed about its periphery. Such bead is captured between the her adapter 16 and the proximal edge of the tubular section 28. Grooves are formed in these respective elements to ensure a positive grasp of the bead element 66. The position of the bead 66 relative its point of attachment to the taper lock section 50, and the sizing of the diaphragm 64 ensure that the diaphragm is pre-loaded such that it biases the tapered shoulder 56 of the piston 46 into contact with the taper lock section 42 of the adapter 16.

Turning now to a more detailed discussion of the operation of the valve shown in the various figures, the dimensions of the elliptical piston head 24 and the marquise-shaped bore 51 are selected such that when the head is constrained into the circular interior of the ANSI her taper section 38 of the luer adapter 16, the bore is completely collapsed to tightly close off the orifice 26 and cause the adjacent lips 54 of the taper lip seal 59 to abut one another. The tapered shoulder 56 of the taper lock section 50 contacts the ramp/lock section 42 of the adapter 16 and prevents the top of the piston head 24 from extending beyond the connection port 18. The internal diameter of the center section 40 of the her adapter 16 is selected such that the piston head 24 is free to assume its elliptical shape when positioned therein. This, in turn, allows the bore 51 to reassume its natural marquise-shape thereby opening a fluid path through the piston and the connector.

Referring now to the embodiments shown in FIGS. 2–11, the needleless connector is initially in its unaccessed state or dosed position as shown in FIG. 2, 4, 11a, and 11b. The compressible section 48 is pre-loaded and causes the piston head 24 to be biased into the ANSI luer taper section 38 (FIG. 6) of the luer adapter 16. The shoulder 56 of the taper-lock section 50 contacts the tapered ramp/lock section 42 of the adapter 16 and prevents the top of the piston head 24 from extending beyond the connection orifice 18 to form a smooth and flush surface. The bore 51 throughout the piston head 24 is tightly squeezed shut by virtue of the normally elliptically shaped piston head being constrained into the circular cross-section of the ANSI luer taper section 38. The sharp pointed ends of the marquise-shaped bore facilitate a tight seal upon compression of the bore along its minor axis by compression of the piston head 24 along its major axis. The taper lips 54 of the taper lip seal 59 or, alternatively, the flexible flaps 55 shown in FIG. 9 further ensure that the bore 51 remains sealed even when subjected to substantial internal pressures. The diaphragm element 64 employed in the alternative embodiment shown in FIGS. 12 and 13 similarly serves to bias the piston head 24 into the ANSI luer taper section of adapter 16.

Just prior to accessing the connector, the piston head 24 and the edge of the connection port 18 are cleaned by, for example, passing a sterilizing swipe over the smooth surface. The absence of ridges, grooves, gaps, or protrusions ensure that proper cleanliness is achieved. The connector is then ready to be accessed by a standard male luer with or without a luer lock.

As the male luer tip 62 of the male luer connector 60 (FIGS. 3, 5, 8, and 13) is brought into contact with the top surface of the rubber piston head 24, a seal is formed to preclude the passage of liquid or air therebetween. The application of sufficient pressure causes the compressible section 48 of the piston element 44 to compress or, alternatively, diaphragm 64 to stretch, and the piston head 24 to be moved out of the ANSI luer taper section 38 and into the center section 40 (FIG. 6). As the piston head clears the tapered ramp/stop section 42 and is moved into the center section 40, its larger internal diameter allows the piston head to assume is naturally elliptical open shape. This, in turn, allows the bore 51 to assume its natural marquise-shape thereby opening a fluid path through the piston head. Continued pressure by the male luer causes the piston head to be advanced into the tubular section 28 of the main body 14.

In FIGS. 8a and 8b, the slightly reduced inner diameter of the tubular section 28 relative to the diameter of the center section 40 of the adapter 16 serves to further enlarge the orifice 26 of the bore 51 by forcing rubber material up around the outside of the male tip 60. The hooks 25 formed in the bottom edge of the taper lock section 50 engage an annular groove 35 to positively pull the bore 51 open. The center section 40 of the luer adapter 16 may be formed to have an elliptical shape wherein is minor axis is sized slightly smaller than the minor axis of the piston head 24. This serves to compress the piston head along its minor axis further ensuring that the bore attains its fully opened shape. In the alternative embodiment shown in FIGS. 11a and 11b, slight penetration of the rounded tip 61 of the post 63 into the bore 51 positively ensures the opening of the bore. The fact that the tip is rounded and of relatively small diameter prevents it from damaging the piston. It has been found that the embodiment of the post 63 shown does not cut, tear, or cause a punching action on the piston when the piston is moved into contact with the post 63.

In this position, the connector is fully accessed to provide a short, straight, unobstructed fluid path through the connector. At no time does fluid flow about the outside of the piston element on its way through the connector. A "residual" volume, i.e., the volume between the male luer and the exit orifice, of as little as 0.04 ml is attainable. Air leakage, or the entry of contamination, as well as the escape of fluid from the device, is precluded at all times.

In the embodiment shown in FIGS. 2 and 3 and the alternative embodiment shown in FIGS. 11a, 11b, the support tube 29, and the center post 63, respectively, serve to prevent the compressible section 48 from buckling and closing off the fluid path. The flattened cross-sectional shape of the post 63 ensures adequate clearance adjacent the compressed accordioned section 48 to provide for flow at all times. In the embodiment shown in FIG. 3, fluid is directed through the center of the support tube 29.

As the male luer is withdrawn, the biasing force generated by the compressible section 48 of the piston element 44, or the stretchable diaphragm 64 of the alternative embodiment shown in FIGS. 12 and 13, maintains contact between the piston head 24 and the male luer tip 62. The slightly larger diameter of the center section 40 of the luer adapter 16 (FIG. 6) relative to the tubular section 28 causes the piston taper-lock section 50 to freely move into position with the shoulder 56 (FIG. 7a) abutting the ramp/lock section 42 (FIG. 6). Simultaneously, the elliptical piston head 24 is guided into the ANSI luer taper section 38 by the tapered ramp/lock section 42 where it is once again forced into the constrained circular shape of the ANSI luer taper section to close off the bore 51 and reestablish a positive seal. A similar operation occurs with the embodiment shown in FIGS. 12 and 13.

While particular forms of the invention have been illustrated and described, it will also be apparent to those skilled in the art that various modifications can be made without departing from the spirit and scope of the invention. Accordingly, it is not intended that the invention be limited except by the appended claims.

What is claimed is:

1. A needleless connector valve comprising:
   a hollow housing having a connection port and exit orifice wherein the housing includes a first section of a first preselected cross-sectional shape and size disposed directly adjacent the connection port and a second section of a second preselected cross-sectional shape and size situated adjacent the first section;
   a resiliently deformable piston head, having a bore formed therethrough, received within the housing so as to be shiftable between the first and second sections, wherein positioning of the piston head within the first section causes it to be deformed so as to occlude the bore while positioning of the piston head within the second section allows the piston head to assume its un-deformed state in which the bore is un-occluded to thereby provide a fluid path between the connection port and the exit orifice; and
   means for biasing the piston head into the first section to close off the fluid path.

2. The needleless connector valve of claim 1 wherein the piston head is elliptical in cross-section, and the first section of the housing is circular in cross-section.

3. The needleless connector valve of claim 2 wherein the bore formed in the piston head has a marquise-shaped cross-section having its major axis oriented perpendicularly to the major axis of the elliptical cross-section of the piston head.

4. The needleless connector valve of claim 3 wherein the second section of the housing is circular in cross-section and wherein the diameter of the second section is greater than the diameter of the first section.

5. The needleless connector valve of claim 4 wherein a frustoconical section separates the first and second sections of the housing, and wherein the piston head has a taper-lock section extending distally therefrom that conforms to the frustoconical section so as to limit proximal movement of the piston head to a position flush with the surrounding connection port.

6. The needleless connector valve of claim 1 wherein the biasing means comprises a hollow resiliently collapsible member extending distally from the piston head and sealingly seated about the exit orifice.

7. The needleless connector valve of claim 6 wherein the hollow collapsible member comprises a fluid path between the piston head and the exit orifice.

8. The needleless connector valve of claim 7 wherein a taper-lock section of circular cross-section is disposed between the piston head and the resiliently collapsible member.

9. The needleless connector valve of claim 8 wherein a section elliptical and conical in shape is positioned between said piston head and said taper-lock section.

10. The needleless connector valve of claim 9 wherein the piston head, the taper-lock section and the resiliently collapsible member comprise a single rubber molding.

11. The needleless connector valve of claim 10 wherein a taper lip seal is formed about the distal end of the bore.

12. The needleless connector valve of claim 1 wherein the connection port is dimensioned to receive a male luer.

13. The needleless connector valve of claim 12 wherein the housing includes means for enabling the luer to lock thereto.

14. A needleless connector valve, comprising:

a hollow housing having a connection port and an exit orifice wherein the housing includes a first section of circular cross-section having a first diameter disposed directly adjacent the connection port and a second section of circular cross-section having a second diameter larger than the first diameter disposed adjacent the first section;

a resiliently deformable piston head of elliptical cross-section, having a bore formed therethrough oriented along is longitudinal axis, received within the housing so as to be shiftable between the first and second sections, wherein positioning of the piston head in the first section causes it to be deformed so as to have a circular cross-section thereby occluding the bore extending therethrough while positioning of the piston head in the second section allows it to assume is un-deformed elliptical shape in which the bore extending therethrough is un-occluded to thereby provide a fluid path between the connection port and the exit orifice; and means for biasing the piston head into the first section to close off the fluid path whereby insertion of a fluid conduit device into the connection port serves to shift the piston head into the second section to open the fluid path.

15. The needleless connector valve of claim 14 wherein the bore formed in the piston has an elliptical cross-section having its major axis perpendicularly oriented relative the major axis of the elliptical cross-section of the piston head.

16. The needleless connector valve of claim 15 wherein the biasing means comprises a hollow resiliently collapsible member extending distally from the piston head and sealingly seated about the exit orifice.

17. The needleless connector valve of claim 16 wherein the biasing means comprises an accordioned structure.

18. The needleless connector valve of claim 17 wherein the piston head and the resiliently collapsible member comprise a single rubber molding.

19. The needleless connector valve of claim 18 further comprising a taper lip seal positioned about the distal end of the bore extending through the piston head.

20. The needleless connector valve of claim 18 wherein the piston head has a flat proximal surface, and further comprising means to limit movement of the piston head in a proximal direction to a position wherein the flat surface is flush with the connection port.

21. The needleless connector valve of claim 18 wherein the collapsible member is hollow and provides a fluid path between the piston head and the exit orifice.

22. The needleless connector valve of claim 21 wherein the connection port is dimensioned to receive a male luer.

23. The needleless connector valve of claim 22 wherein the housing includes means for enabling the luer to lock thereto.

24. A valve mechanism for incorporation within a connector device having a bore formed therein extending between a connection port and an exit orifice, wherein the bore has a first section of reduced diameter directly adjacent the connection port and a second section of enlarged diameter distally adjacent the first section, comprising:

a resiliently deformable piston head of elliptical cross-section having a bore extending therethrough, wherein the piston head is disposed within the connector device so as to be shiftable between the first and second sections, and wherein positioning the piston head within the first section causes it to be deformed to a circular shape to occlude the bore extending therethrough while positioning the piston head in the second section allows the piston head to assume its un-deformed elliptical shape wherein the bore is un-occluded to provide a fluid path from the connection port to the exit orifice;

means for biasing the piston head to position in the first section to close off the fluid path whereby insertion of a fluid conduit device into the connection port serves to shift the piston head into the second section to open the fluid path.

25. The valve mechanism of claim 24 wherein the bore extending through the piston head is marquise-shaped in cross-section having a major axis oriented perpendicularly relative the major axis of the elliptical piston head.

26. The valve mechanism of claim 25 wherein the bias means comprises a resiliently collapsible extension of the piston head.

27. The valve mechanism of claim 26 wherein the collapsible extension is hollow to provide a fluid path between the piston head and the exit orifice.

28. The valve mechanism of claim 26 further comprising means for preventing the biasing means from extending the piston head beyond a position flush with the connection port.

29. The valve mechanism of claim 26 further comprising a taper lip seal positioned about the distal end of the bore extending through the piston head.

* * * * *

UNITED STATES PATENT AND TRADEMARK OFFICE
CERTIFICATE OF CORRECTION

PATENT NO. : 5,676,346
DATED : Oct. 14, 1997
INVENTOR(S) : Karl R. Leinsing

It is certified that error appears in the above-identified patent and that said Letters Patent is hereby corrected as shown below:

Front page, below ABSTRACT description, Change "29 Claims", To read --49 Claims--.

IN THE CLAIMS:
    Add the following claims.

--30. The needleless connector valve of claim 1 wherein the bore formed in the piston head is marquise-shaped.

31. The needleless connector valve of claim 1 wherein the biasing means comprises a resilient bellows disposed between the housing and the piston head such that the bellows urges the piston head to the first section of the housing.

UNITED STATES PATENT AND TRADEMARK OFFICE
CERTIFICATE OF CORRECTION

PATENT NO. : 5,676,346
DATED : Oct. 14, 1997
INVENTOR(S) : Karl R. Leinsing

It is certified that error appears in the above-identified patent and that said Letters Patent is hereby corrected as shown below:

32. The needleless connector valve of claim 1 wherein the piston head and the biasing means are formed as one piece with the biasing means comprising a resilient bellows mounted in the second section of the housing to urge the piston head into the first section of the housing.

33. The needleless connector valve of claim 1 further comprising limiting means for preventing the piston head from extending beyond a position flush with the connection port.

34. The needleless connector of claim 33 wherein the limiting means comprises:
        a lock section formed in the housing;
        a lock portion formed on the piston shaped to mate with the lock section of the housing;

UNITED STATES PATENT AND TRADEMARK OFFICE
CERTIFICATE OF CORRECTION

PATENT NO. : 5,676,346
DATED : Oct. 14, 1997
INVENTOR(S) : Karl R. Leinsing

It is certified that error appears in the above-identified patent and that said Letters Patent is hereby corrected as shown below:

wherein the lock portion of the piston mates with the lock section of the housing when the piston is located in the first section of the housing thereby limiting the piston from extending beyond the flush position with the connection port.

35. The needleless connector valve of claim 1 wherein the piston head further comprises a transition section having an elliptical shape oriented so as to apply force to the piston head to open the bore when the piston head is located in the second section of the housing.

36. The needleless connector valve of claim 35 wherein the transition section further comprises a conically-shaped segment located so as to apply force to the piston head to open the bore when the piston

UNITED STATES PATENT AND TRADEMARK OFFICE
CERTIFICATE OF CORRECTION

PATENT NO. : 5,676,346
DATED : Oct. 14, 1997
INVENTOR(S) : Karl R. Leinsing

It is certified that error appears in the above-identified patent and that said Letters Patent is hereby corrected as shown below:

head is located in the second section of the housing.

37. The needleless connector valve of claim 1 wherein the bore formed in the piston head is marquise-shaped and the piston head further comprises a taper lip seal formed about the distal end of the bore.

38. The needleless connector valve of claim 9 wherein the elliptical and conical sections positioned between the piston head and the taper-lock section are oriented so as to apply force to the piston head to open the bore when the piston head is located in the second section of the housing.

UNITED STATES PATENT AND TRADEMARK OFFICE
CERTIFICATE OF CORRECTION

PATENT NO. : 5,676,346
DATED : Oct. 14, 1997
INVENTOR(S) : Karl R. Leinsing

It is certified that error appears in the above-identified patent and that said Letters Patent is hereby corrected as shown below:

39. The needleless connector valve of claim 14 wherein the piston head further comprises a transition section having an elliptical shape oriented so as to apply force to the piston head to open the bore when the piston head is located in the second section of the housing.

40. The needleless connector valve of claim 39 wherein the transition section further comprises a conically-shaped segment located so as to apply force to the piston head to open the bore when the piston head is located in the second section of the housing.

41. The needleless connector valve of claim 14 wherein the biasing means comprises a resilient bellows disposed between the housing and the piston

UNITED STATES PATENT AND TRADEMARK OFFICE
CERTIFICATE OF CORRECTION

PATENT NO. : 5,676,346
DATED : Oct. 14, 1997
INVENTOR(S) : Karl R. Leinsing

It is certified that error appears in the above-identified patent and that said Letters Patent is hereby corrected as shown below:

head such that the bellows urges the piston head to the first section of the housing.

42. The needleless connector valve of claim 14 wherein the piston head and the biasing means are formed as one piece with the biasing means comprising a resilient bellows mounted in the second section of the housing to urge the piston head into the first section of the housing.

43. The needleless connector valve of claim 14 further comprising limiting means for preventing the piston head from extending beyond a position flush with the connection port.

44. The needleless connector of claim 43 wherein the limiting means comprises:

UNITED STATES PATENT AND TRADEMARK OFFICE
CERTIFICATE OF CORRECTION

PATENT NO. : 5,676,346
DATED : Oct. 14, 1997
INVENTOR(S) : Karl R. Leinsing

It is certified that error appears in the above-identified patent and that said Letters Patent is hereby corrected as shown below:

a lock section formed in the housing;

a lock portion formed on the piston shaped to mate with the lock section of the housing;

wherein the lock portion of the piston mates with the lock section of the housing when the piston is located in the first section of the housing thereby limiting the piston from extending beyond the flush position with the connection port.

45. The valve mechanism of claim 24 wherein the biasing means comprises a resilient bellows disposed between the housing and the piston head such that the bellows urges the piston head to the first section of the housing.

46. The valve mechanism of claim 24 wherein the piston head and the biasing means are formed as

UNITED STATES PATENT AND TRADEMARK OFFICE
CERTIFICATE OF CORRECTION

PATENT NO. : 5,676,346
DATED : Oct. 14, 1997
INVENTOR(S) : Karl R. Leinsing

It is certified that error appears in the above-identified patent and that said Letters Patent is hereby corrected as shown below:

one piece with the biasing means comprising a resilient bellows mounted in the second section of the housing to urge the piston head into the first section of the housing.

47. The valve mechanism of claim 24 wherein the piston head further comprises a transition section having an elliptical shape oriented so as to apply force to the piston head to open the bore when the piston head is located in the second section of the housing.

48. The valve mechanism of claim 47 wherein the transition section further comprises a conically-shaped segment located so as to apply force to the

UNITED STATES PATENT AND TRADEMARK OFFICE
CERTIFICATE OF CORRECTION

PATENT NO. : 5,676,346
DATED : Oct. 14, 1997
INVENTOR(S) : Karl R. Leinsing

It is certified that error appears in the above-identified patent and that said Letters Patent is hereby corrected as shown below:

piston head to open the bore when the piston head is located in the second section of the housing.

49. The valve mechanism of claim 28 wherein the preventing means comprises:
  a lock section formed in the housing;
  a lock portion formed on the piston shaped to mate with the lock section of the housing;
  wherein the lock portion of the piston mates with the lock section of the housing when the piston is located in the first section of the housing thereby limiting the piston from extending beyond the flush position with the connection port.--

Signed and Sealed this

Tenth Day of March, 1998

Attest:

BRUCE LEHMAN

Attesting Officer

Commissioner of Patents and Trademarks